United States Patent [19]

Bucalo

[11] 4,054,138
[45] Oct. 18, 1977

[54] IMPLANTS FOR ACTING ON LIVING BEINGS

[76] Inventor: Louis Bucalo, 155 Roberts St., Holbrook, N.Y. 11741

[21] Appl. No.: 685,636

[22] Filed: May 12, 1976

Related U.S. Application Data

[62] Division of Ser. No. 537,572, Dec. 30, 1974, Pat. No. 3,982,537.

[51] Int. Cl.² .......................................... G61M 31/00
[52] U.S. Cl. ..................................................... 128/260
[58] Field of Search ............... 128/260, 235, 261, 272, 128/271; 424/19, 180

[56] References Cited

U.S. PATENT DOCUMENTS

| | | | |
|---|---|---|---|
| 3,489,147 | 1/1970 | Shaw | 128/218 |
| 3,756,390 | 9/1973 | Abbey | 128/272.1 X |
| 3,760,805 | 9/1973 | Higuchi | 128/260 |
| 3,760,984 | 9/1973 | Theeuwes | 128/260 |
| 3,773,919 | 11/1973 | Boswell | 128/260 |
| 3,777,755 | 12/1973 | Groves | 128/271 |
| 3,875,939 | 4/1975 | Bolduc | 128/235 |
| 3,982,537 | 9/1976 | Bucalo | 128/260 |

Primary Examiner—Aldrich F. Medbery
Attorney, Agent, or Firm—Steinberg & Blake

[57] ABSTRACT

Implants which are adapted to be implanted in the interior tissue of a living being such as a human being, animal or the like and there acting on the health of said living being over a prolonged period of time by slowly releasing a substance which acts on the health of the living being while being absorbed by the living being. Implants of this type include a substance which is implanted in liquid molten condition into the internal tissue of the living being and which there solidifies, said substance being safely absorbable by the living being and being solid at the temperature of the body of the living being while being molten and liquid at a higher temperature at which it is implanted but which temperature does not adversely affect the living being during the implanting, the substance having distributed therethrough an agent which affects the health of a living being so that as said substance is absorbed by the living being the agent is released within the internal tissues to act on the health of the living being. The invention further includes packages of the implant.

5 Claims, 5 Drawing Figures

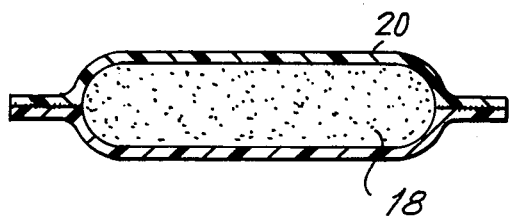
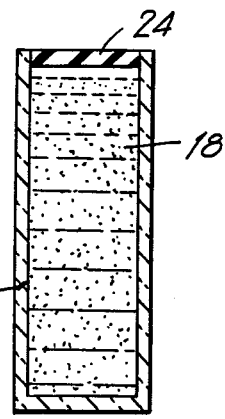
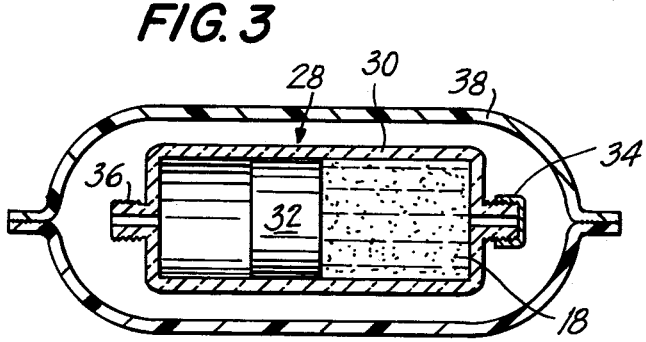
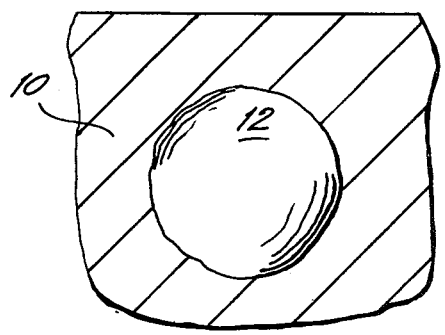
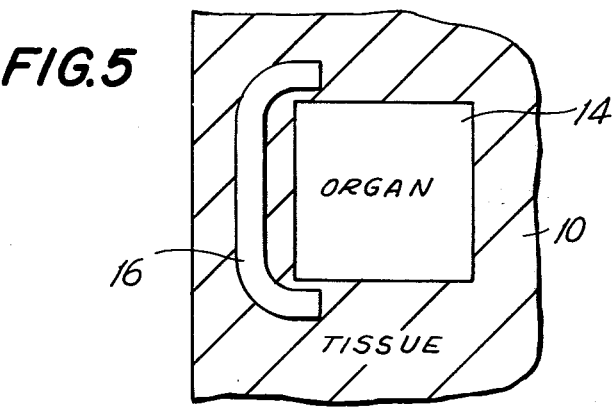

IMPLANTS FOR ACTING ON LIVING BEINGS

CROSS REFERENCE TO RELATED APPLICATION

This application is a divisional of my Ser. No. 537,572 filed Dec. 30, 1974, entitled "Dynamic Implants and Method for Implanting the Same", now patent No. 3,982,537.

BACKGROUND OF THE INVENTION

The present invention relates to implants for use with subjects such as human beings, animlas, or the like.

Thus, while the present invention is particularly designed for use with human beings and other mammals, it is also possible to visualize situations where the present invention may have utility with birds, fish, reptiles, etc.

One of the problems encountered with subjects of this type is the problem of administering to such subject medicinal agents such as antibiotics, drugs, and the like, in a predetermined dosage and over a relatively long interval. At the present time, considerable inconvenience and disadvantages are involved in administering such agents. For example, such agents may be taken orally or they may be injected into the body, but such oral administration and injections must be repeated from time to time, and initially when such agents are administered in such conventional manners the subject receives a relatively large concentrated dose which gradually disappears until another large dose is administered to again undesirably raise the level at which the medicinal agent is received by the body, with the rate of administering the agent to the body gradually diminishing until the next injection or oral administration.

A further problem encountered with subjects of the above type is in connection with localizing the administering of the required agent in such a way that the desired agent will be surely received by the part of the subject requiring the agent. At the present time certain medicinal agents are distributed throughout the entire body although it is only required that they be received by a particular part of the subject.

SUMMARY OF THE INVENTION

It is accordingly a primary object of the present invention to provide compositions and structures for avoiding the above drawbacks.

In particular, it is an object of the present invention to provide for subjects of the above type an implant which is capable of being absorbed by the tissue of the subject while slowly releasing an agent to act on the subject.

Furthermore, it is an object of the present invention to provide an implant of this type which is capable of releasing to the tissue, while the absorbable substance gradually disappears, agents which will affect the health of a subject.

Furthermore, it is an object of the present invention to provide an implant capable of releasing an agent in a localized manner according to which the agent will reliably be received by a part of the body for which it is intended without necessitating general administration of such an agent throughout the body.

Furthermore, it is an object of the present invention to provide implants of the above type which are capable of being packaged and sold in such a way that they are convenient to use and will have a long shelf life.

Generally speaking in accordance with the present invention there is provided for implant purposes a substance which is safely absorbable by a living being and which is solid at the temperature of the body of said living being while being molten and liquid at a higher temperature at which the substance can be implanted into the living being, the implanting temperature not adversely affecting the living being during the implanting, said substance having distributed therethrough an agent which affects the health of said living being so that after implant a depot is formed of said substance having said agent distributed therethrough and as said substance is abosrbed by the living being the agent is released within the internal tissue of the living being to there act on its health. The term "molten and liquid" as used herein does not mean that the substance must be as free flowing as water, for example. So long as the substance is sufficiently fluid to be injected, it is covered by this term, so that highly viscous substances are also covered provided that the same can be injected to form a depot.

BRIEF DESCRIPTION OF DRAWINGS

The invention is illustrated by way of example in the accompanying drawings which form part of this application and in which:

FIG. 1 is a schematic illustration of a package containing a particulate material which may form part of an implant of the invention;

FIG. 2 is a schematic sectional elevation showing another type of container for containing implantable particulate material which is suspended in a suitable liquid carrier;

FIG. 3 is a schematic sectional elevation of part of a syringe which may be used for implanting in accordance with the present invention;

FIG. 4 is a schematic illustration of an implant of the invention situated in tissue; and FIG. 5 is a schematic illustration of another type of implant situated in tissue.

DESCRIPTION OF PREFERRED EMBODIMENTS

In accordance with one of the methods of the present invention, an absorbable substance is injected into the interior tissue of a subject such as a human being, animal, or the like. Thus, FIG. 4 shows internal tissue 10 having a body of absorbable substance 12 according to the present invention implanted therein. This substance 12 which forms at least part of the implant shown in FIG. 4 is a substance which is solid at body temperature but which is liquid and molten at a temperature above body temperature at which it may be implanted in the living being, and may, for example, be a hydrogenated vegetable oil or a hydrogenated animal fat, the latter substances having the property of being solid at body temperature while at the same time they are gradually absorbed by the tissue of the body so that the implant 12 of FIG. 4 will gradually reduce in size.

In the case of the use of solids such as hydrogenated vegetable oil or animal fats, such solids may be made to have a melting temperature which is somewhat higher than body temperature such as the temperature on the order of 130° F. Thus, in order to provide such an implant is is only necessary to melt the substance while it is at an elevated temperature in liquid form it is implanted as by being injected with a suitable syringe and while the injected substance cools to body temperature it will solidify. This substance carries the agent which affects the health of the living being distributed therethrough, as for example a drug, vitamin, etc.

An injectable substance of this latter type has a temperature which is not so much higher than the body temperature when the substance is in liquid form as to create an undesirable pain when injected. However, if desired the needle of the syringe can be covered with a suitable insulating layer to insulate the tissue from the liquid hydrogenated oil or animal fat which is at elevated temperature while it is injected.

The present invention provides the important advantage of permitting dispersal through the absorbable substance of a suitable agent such as a drug or antibiotic having medicinal properties, so that with the present invention it becomes possible to continuously release such an agent through the tissue to the body at a predetermined steady rate. For this purpose, when a substance such as hydrogenated vegetable oil or animal fat is melted, an agent of the above type is added to the molten substance, and then such substance can be injected in the manner described above.

Referring to FIG. 5, it will be seen that in the tissue 10 there is a diagrammatically illustrated organ 14 which may be any of the organs of the body. While the substance of the above type with an agent dispersed therethrough is still in liquid form, it can be injected so as to provide a casting 16 as illustrated in FIG. 5. Thus the injection can easily be carried out in such a way that the injected substance will become closely located along and around an organ 14 or the like so that the agent which is released will directly affect the organ which is intended to receive the agent without necessitating general administering of the agent throughout the body.

It is also possible in accordance with the present invention instead of injecting a substance of the above type in liquid condition to heat the substance to liquid form for the purpose of adding the desired agent thereto and then solidifying the substance. This solidified substance can then be crushed into a particulate form such as the form of a suitable powder. However, in order to achieve a powder of this latter type it is preferred to spray the substance which has the agent dispersed therethrough with a suitable inert gas spray which will provide fine droplets which solidify while cooling in the inert gas to form in this highly effective manner a fine powder. The particles of such powder will of course also be absorbable by the body while having an agent of the above type dispersed therethrough.

As may be seen from FIG. 1, such a powder 18 may be situated in a suitable package 20 made of polyethylene or the like and suitably lined with a film of aluminum or the like so that a long shelf life is assured. If desired the interior of the package may be provided with a suitable atmosphere such as an atmosphere of carbon dioxide.

When it is desired to use the particles as shown in FIG. 1 they may be placed in a suitable liquid carrier such as a suitable saline solution or a gelatin solution. The use of liquid hydrogenated vegetable oil or the like which is liquid at room temperature is less desirable because the solid particles will partly dissolve in such liquid. Thus, by situating the particles 18 in a carrier in which the particles will not dissolve it is possible for these solids to remain in the body for a long period of time gradually releasing the agent to the tissue of the body. The carrier is absorbed more rapidly than the solids carried thereby and these solids may take the form of superfine particles or it is also possible to have a liquid agent which will gradually dissolve while being carried by a suitable carrier. Such liquid agent may be in the form of fine droplets dispersed through a solid carrier.

Thus, FIG. 2 shows a container 22 in the form of a suitable vial which may be closed at its top end by a rubber closure element 24. Within this vial 22 is located a carrier liquid such as a saline solution which has dispersed therethrough the particles 18. Thus, FIG. 2 shows a suitable package for the invention. With this package the needle of the syringe need only be punctured through the cover 24 so as to draw into the syringe a liquid carrier with the particles of the invention therein and then the injection can be made at a desired location.

Inasmuch as particles of the type referred to above, when suspended in a suitable liquid carrier, may be difficult to inject with a conventional syringe, it is possible according to a further feature of the invention to package the liquid carrier and the particles of the invention suspended therein in a syringe of the type shown in FIG. 3. Thus, FIG. 3 shows a syringe 28 having an elongated cylindrical barrel 30 in which a piston 32 is slidable. The barrel 30 is provided at its right end as viewed in FIG. 3 with a threaded opening closed by a suitable cap 34 and capable of having a hollow needle attached thereto just prior to the injection of the liquid carrier and particles suspended therein, the liquid carrier and particles 18 suspended therein being housed within the syringe between the piston 32 and the cap 34 in the manner shown in FIG. 3.

The opposite end of the barrel 30 is provided with a suitable fitting 36 capable of being attached to any suitable source of air under pressure. Thus; with such a syringe the air under pressure. Thus, with such a syringe the air pressure will be introduced into the barrel through the fitting 36 behind the piston 32 in order to drive the latter for discharging the contents of the syringe into the body tissue. The entire syringe structure 28 can be housed within a suitable package 38 similar to the package 20 of FIG. 1.

As was pointed out above, the agents which are dispersed through the absorbable substance of the invention may be medicinal agents such as suitable drugs, antibiotics or the like. Thus, penicillin, for example, may be such an agent, and other possible agents are steroids such as cortisone, as well as anabolic steroids, estrogenic steroids, etc. Moreover, it is possible to visualize circumstances when nutrient or vitamin agents are dispersed through the absorbable substance so as to be released to the tissue of the body.

While the invention has been described in particular with respect to specific structures and methods, it is apparent that variations and modifications of the invention can be made.

What is claimed is:

1. An implantable composition for treating a living being over a prolonged period of time with an agent which affects the health of such living being by causing said agent to be slowly released during said period of time within internal tissues of the living being, comprising an absorbable carrier substance which solidifies in the internal tissue of the living being and which is safely absorbable by the living being, said substance being solid at the temperature of the body of said living being and being molten and liquid at a higher temperature at which it can be implanted, the implanting temperature being such as to adversely affect the living being during the implanting, said substance having distributed therethrough said agent which affects the health of said living being so that as said substance is absorbed by the living being the agent is released within the internal tissue of the living being to act on its health.

2. Composition according to claim 1 wherein said substance is a hydrogenated vegetable oil, animal fat, or the like.

3. Composition according to claim 2 wherein said substance is hydrogenated cottonseed oil.

4. Composition according to claim 1 wherein said agent is an antibiotic.

5. Composition according to claim 1 wherein said agent is a drug.

* * * * *

UNITED STATES PATENT AND TRADEMARK OFFICE
CERTIFICATE OF CORRECTION

PATENT NO. : 4,054,138
DATED : October 18, 1977
INVENTOR(S) : LOUIS BUCALO

It is certified that error appears in the above–identified patent and that said Letters Patent are hereby corrected as shown below:

Column 5, line 1, after "to" insert --not--.

Signed and Sealed this

Seventh Day of February 1978

[SEAL]

Attest:

RUTH C. MASON
*Attesting Officer*

LUTRELLE F. PARKER
*Acting Commissioner of Patents and Trademarks*